US012290326B2

(12) United States Patent
Qian et al.

(10) Patent No.: US 12,290,326 B2
(45) Date of Patent: May 6, 2025

(54) VIRTUAL INTERACTION WITH INSTRUMENTS IN AUGMENTED REALITY

(71) Applicant: Medivis, Inc., New York, NY (US)

(72) Inventors: Long Qian, Brooklyn, NY (US); Christopher Morley, New York, NY (US); Osamah Choudhry, New York, NY (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 18/583,328

(22) Filed: Feb. 21, 2024

(65) Prior Publication Data

US 2024/0189044 A1 Jun. 13, 2024

Related U.S. Application Data

(63) Continuation of application No. 17/489,693, filed on Sep. 29, 2021, now Pat. No. 11,931,114, which is a continuation-in-part of application No. 17/395,233, filed on Aug. 5, 2021, now Pat. No. 11,857,274, and a continuation-in-part of application No. 17/194,191, filed on Mar. 5, 2021, now Pat. No. 11,307,653.

(51) Int. Cl.
| | |
|---|---|
| G06T 19/00 | (2011.01) |
| A61B 34/20 | (2016.01) |
| G06T 17/20 | (2006.01) |
| G16H 40/60 | (2018.01) |

(52) U.S. Cl.
CPC .............. *A61B 34/20* (2016.02); *G06T 17/20* (2013.01); *G06T 19/003* (2013.01); *G06T 19/006* (2013.01); *G16H 40/60* (2018.01); *A61B 2034/2046* (2016.02)

(58) Field of Classification Search
None
See application file for complete search history.

(56) References Cited

U.S. PATENT DOCUMENTS

2020/0184729 A1* 6/2020 Jones ...................... G06F 3/011

OTHER PUBLICATIONS

Wang et al., "Augmented Reality Navigation With Automatic Marker-Free Image Registration Using 3-D Image Overlay for Dental Surgery", 2014. (Year: 2014).*

* cited by examiner

*Primary Examiner* — Nicholas R Wilson
(74) *Attorney, Agent, or Firm* — Cognition IP, P.C.; Edward Steakley; Rajesh Fotedar

(57) ABSTRACT

Various embodiments of an apparatus, methods, systems and computer program products described herein are directed to an Interaction Engine that generates within a unified three-dimensional (3D) coordinate space: (i) a 3D virtual medical model positioned according to a model pose and (ii) at least one virtual object associated with a physical instrument, the physical instrument having a current instrument pose based at least on current coordinates of one or more fiducial markers disposed on the physical instrument, in the unified 3D coordinate space. The Interaction Engine renders an Augmented Reality (AR) display that includes concurrent display of the 3D virtual medical model and the virtual object. The Interaction Engine modifies the AR display according to a virtual interaction related to the virtual object that incorporates the change of the physical instrument pose.

14 Claims, 19 Drawing Sheets

VIRTUAL INTERACTION WITH INSTRUMENTS IN AUGMENTED REALITY

CROSS REFERENCE TO RELATED APPLICATIONS

This application is a continuation of U.S. patent application Ser. No. 17/489,693 entitled "Virtual Interaction With Instruments In Augmented Reality," filed on Sep. 29, 2021, which is a continuation in-part of U.S. patent application Ser. No. 17/194,191 entitled "User Input and Interface Design in Augmented Reality for Use in Surgical Settings," filed on Mar. 5, 2021 and U.S. patent application Ser. No. 17/395,233 entitled "Physical Instrument with Fiducial Markers," filed on Aug. 5, 2021, the contents of which are incorporated by reference in their entirety.

BACKGROUND

Current conventional systems have limitations with regard to two-dimensional (2D) and three-dimensional (3D) images in surgical settings. Surgical planning and surgical navigation are necessary for every medical procedure. A surgeon and their team must have a plan for a case before entering an operating room, not just as a matter of good practice but to minimize malpractice liabilities and to enhance patient outcomes. Surgical planning is often conducted based on medical images including DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

SUMMARY

Various embodiments of an apparatus, methods, systems and computer program products described herein are directed to an Interaction Engine. The Interaction Engine provides significant improvements over the limitations of conventional systems. The Interaction Engine generates within a unified three-dimensional (3D) coordinate space: (i) a 3D virtual medical model positioned according to a model pose and (ii) at least one virtual object associated with a physical instrument, the physical instrument having a current instrument pose based at least on current coordinates of one or more fiducial markers disposed on the physical instrument, in the unified 3D coordinate space. The Interaction Engine renders an Augmented Reality (AR) display that includes concurrent display of the 3D virtual medical model and the virtual object.

The Interaction Engine detects one or more physical gestures associated with the physical instrument. The Interaction Engine identifies a change represented by physical instrument pose data, in the unified 3D coordinate space, due to at least one of the detected physical gestures associated with the physical instrument. The Interaction Engine modifies the AR display according to a virtual interaction related to the virtual object that incorporates the change of the physical instrument pose.

According to various embodiments, the Interaction Engine modifies the AR display according to an offset tip virtual interaction.

According to various embodiments, the Interaction Engine modifies the AR display according to a trajectory virtual interaction.

According to various embodiments, the Interaction Engine modifies the AR display according to a trajectory alignment virtual interaction.

According to various embodiments, the Interaction Engine modifies the AR display according to landmark registration virtual interaction.

According to various embodiments, the Interaction Engine modifies the AR display according to a clipping plane virtual interaction.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

Figure 1A:
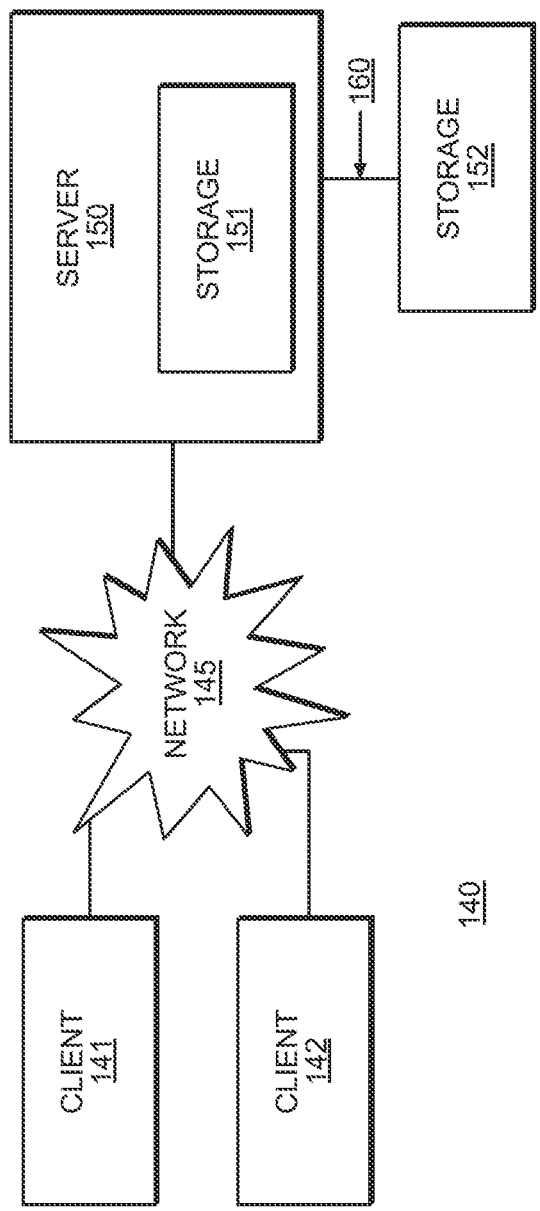
FIG. 1A is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
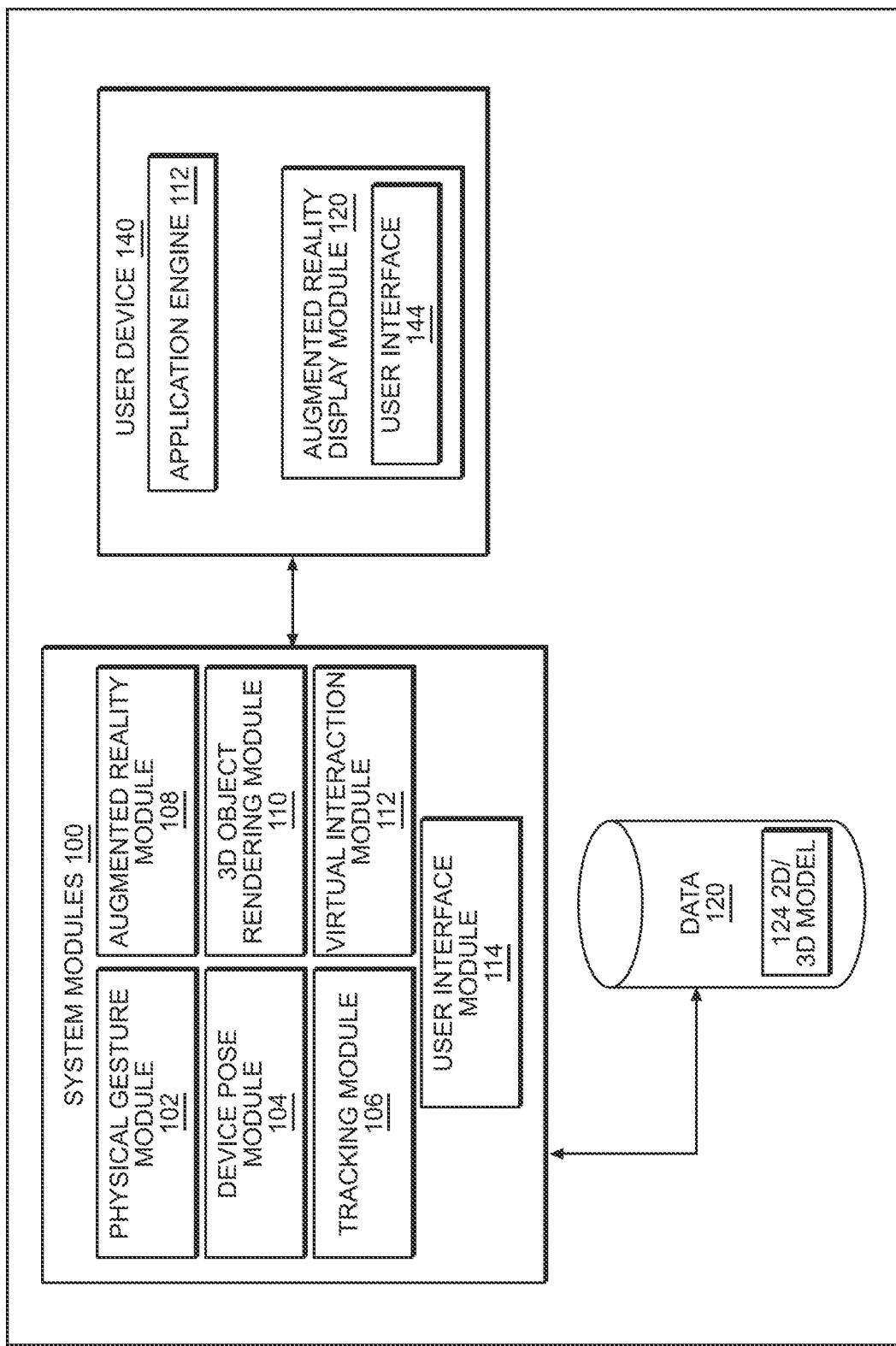
FIG. 1B is a diagram illustrating an exemplary environment in which some embodiments may operate.

FIG. 1B illustrates a block diagram of an example system 100 for an Interaction Engine that includes a physical gesture module 102, a device pose module 104, a tracking module 106, an AR module 108, a 3D object rendering module 110, a virtual interaction module 112 and a user interface module 114. The system 100 may communicate with a user device 140 to display output, via a user interface 144 generated by an application engine 142. In various embodiments, the user device 140 may be an AR display headset device that further includes one or more of the respective modules 102, 104, 106, 108, 110, 112, 114.

The physical gesture module 102 of the system 100 may perform functionality, steps, operations, commands and/or instructions as illustrated in one or more of FIGS. 2A, 2B, 2C, 2D, 3, 4, 5A, 5B, 5C, 5D, 6A, 6B, 7A, 7B, 8A and 8B ("FIGS. 2A-8B").

The device pose module 104 of the system 100 may perform functionality, steps, operations, commands and/or instructions as illustrated in one or more of FIGS. 2A-8B.

The tracking module 106 of the system 100 may perform functionality, steps, operations, commands and/or instructions as illustrated in one or more of FIGS. 2A-8B.

The augmented reality module 108 of the system 100 may perform functionality, steps, operations, commands and/or instructions as illustrated in one or more of FIGS. 2A-8B.

The 3D object rendering module 110 of the system 100 may perform functionality, steps, operations, commands and/or instructions as illustrated in one or more of FIGS. 2A-8B.

The virtual interaction module 112 of the system 100 may perform functionality, steps, operations, commands and/or instructions as illustrated in one or more of FIGS. 2A-8B.

The user interface module 114 of the system 100 may perform functionality, steps, operations, commands and/or instructions as illustrated in one or more of FIGS. 2A-8B.

A database 120 associated with the system 100 maintains information, such as 3D medical model data 124, in a manner the promotes retrieval and storage efficiency and/or data security. In addition, the model data 124 may include rendering parameters, such as data based on selections and modifications to a 3D virtual representation of a medical model rendered for a previous Augmented Reality display. In various embodiments, one or more rendering parameters may be preloaded as a default value for a rendering parameter in a newly initiated session of the Interaction Engine.

In various embodiments, the Interaction Engine accesses one or more storage locations that contain respective portions of medical model data 124. The medical model data 124 may be represented according to two-dimensional (2D) and three-dimensional (3D) medical model data. The 2D and/or 3D ("2D/3D") medical model data 124 may include a plurality of slice layers of medical data associated with external and internal anatomies. For example, the 2D/3D medical model data 124 may include a plurality of slice layers of medical data for generating renderings of external and internal anatomical regions of a user's head, brain and skull. It is understood that various embodiments may be directed to generating displays of any internal or external anatomical portions of the human body and/or animal bodies.

The Interaction Engine renders the 3D virtual medical model in an AR display based on the 3D medical model data. In addition, the Interaction Engine renders the 3D virtual medical model based on model pose data which describes an orientation and position of the rendering of the 3D virtual medical model. The Interaction Engine applies the model pose data to the 3D medical model data to determine one or more positional coordinates in the unified 3D coordinate system for portion(s) of model data of a slice layer(s) that represent various anatomical locations.

The Interaction Engine further renders the 3D virtual medical model based on a current device pose of an AR headset device worn by the user. The current device pose represents a current position and orientation of the AR headset device in the physical world. The Interaction Engine translates the current device pose to a position and orientation within the unified 3D coordinate system to determine the user's perspective view of the AR display. The Interaction Engine generates a rendering of the 3D virtual medical model according to the model pose data for display to the user in the AR display according to the user's perspective view. Similarly, the Interaction Engine generates instrument pose data based on a current pose of a physical instrument. The current instrument pose represents a current position and orientation of a physical instrument in the physical world. For example, the physical instrument may be held by a user's hands and may have one or more fiducial markers. The Interaction Engine translates the current instrument pose to a position and orientation within the unified 3D coordinate system to determine the physical instrument's display position and orientation in the AR display and/or placement with respect to one or more virtual objects. It is understood that the Interaction Engine continually updates the instrument pose data to represent subsequent changes in the position and orientation of the physical instrument.

Various embodiments described herein provide functionality for selection of menu functionalities and positional display coordinates. For example, the Interaction Engine tracks one or more physical gestures such as movement of a user's hand(s) and/or movement of a physical instrument (s) via one or more tracking algorithms to determine directional data to further be utilized in determining whether one or more performed physical gestures indicate a selection of one or more types of functionalities accessible via the AR display and/or selection and execution of a virtual interaction(s). For example, the Interaction Engine may track movement of the user's hand that results in movement of a physical instrument and/or one or more virtual offsets and virtual objects associated with the physical instrument. The Interaction Engine may determine respective positions and changing positions of one or more hand joints or one or more portions of the physical instrument. In various embodiments, the Interaction Engine may implement a simultaneous localization and mapping (SLAM) algorithm.

The Interaction Engine may generate directional data based at least in part on average distances between the user's palm and the user's fingers and/or hand joints or distances between portions (physical portions and/or virtual portions) of a physical instrument. In some embodiments, the Interaction Engine generates directional data based on detected directional movement of the AR headset device worn by the user. The Interaction Engine determines that the directional data is based on a position and orientation of the user's hand(s) (or the physical instrument) that indicates a portion (s) of a 3D virtual object with which the user seeks to select and/or virtually interact with and/or manipulate.

According to various embodiments, the Interaction Engine may implement a collision algorithm to determine a portion of a virtual object the user seeks to select and/or virtually interact with. For example, the Interaction Engine may track the user's hands and/or the physical instrument according to respective positional coordinates in the unified 3D coordinate system that correspond to the orientation of the user's hands and/or the physical instrument in the physical world. The Interaction Engine may detect that one or more tracked positional coordinates may overlap (or be the same as) one or more positional coordinates for displaying a particular portion(s) of a virtual object. In response to detecting the overlap (or intersection), the Interaction Engine determines that the user seeks to select and/or virtually interact with the portion(s) of the particular virtual object displayed at the overlapping positional coordinates.

According to various embodiments, upon determining the user seeks to select and/or virtually interact with a virtual object, the Interaction Engine may detect one or more changes in hand joint positions and/or physical instrument positions and identify the occurrence of the position changes as a performed selection function. For example, a performed selection function may represent an input command to the Interaction Engine confirming the user is selecting a portion of a virtual object via a ray casting algorithm and/or collision algorithm. For example, the performed selection function may also represent an input command to the Interaction Engine confirming the user is selecting a particular type of virtual interaction functionality. For example, the user may perform a physical gesture of tips of two fingers touching to correspond to a virtual interaction representing an input command, such as a select input command.

The Interaction Engine identifies one or more virtual interactions associated with the detected physical gestures. In various embodiments, the Interaction Engine identifies a virtual interaction selected by the user, or to be performed by the user, based on selection of one or more functionalities from a 3D virtual menu displayed in the AR display. In addition, the Interaction Engine identifies a virtual interaction selected by the user according to one or more predefined gestures that represent input commands for the Interaction Engine. In some embodiments, a particular virtual interaction may be identified based on a sequence of performed physical gestures detected by the Interaction Engine. In some embodiments, a particular virtual interaction may be identified as being selected by the user based on a series of preceding virtual interactions.

Figure 2A:
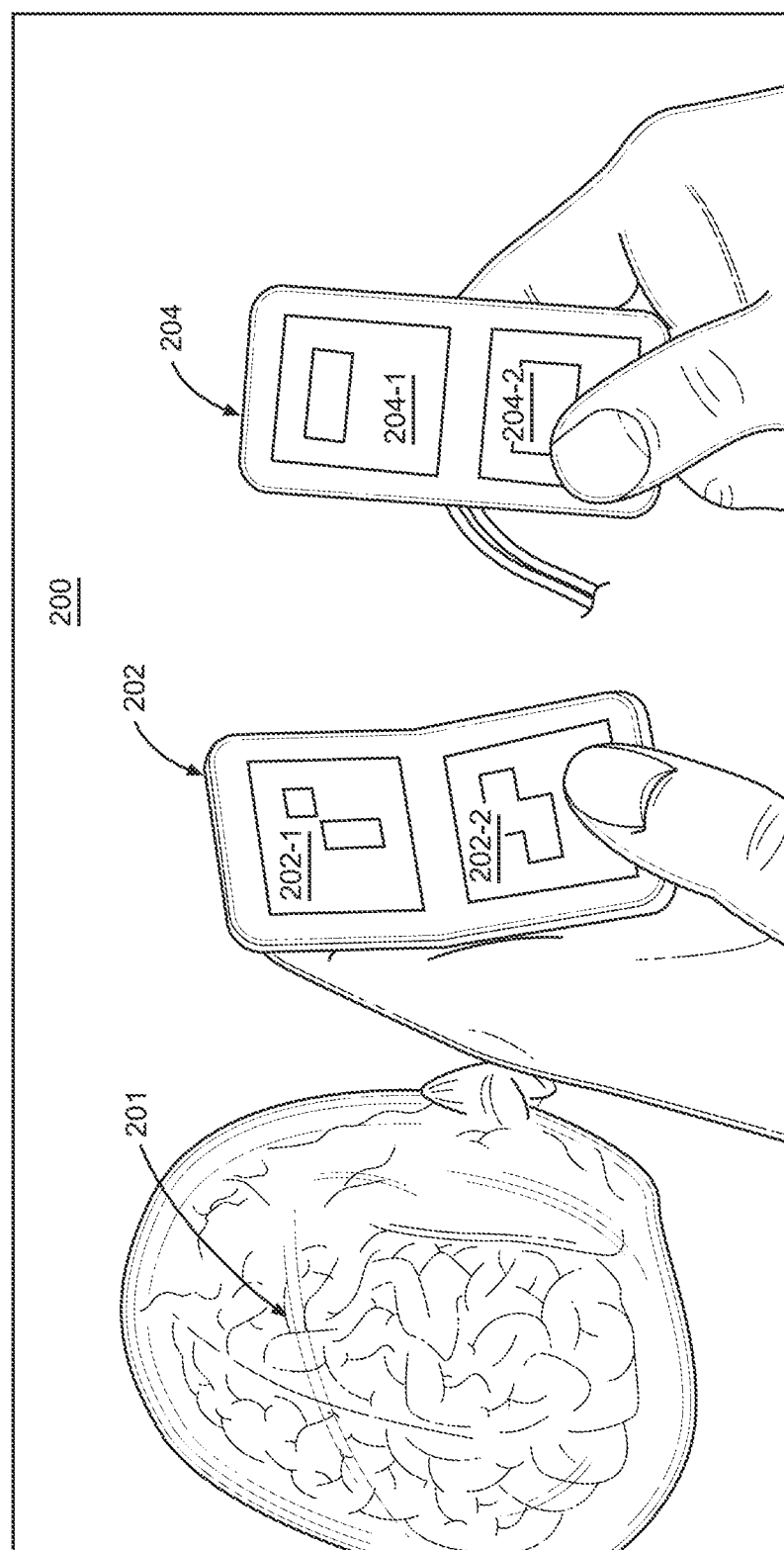
FIGS. 2A, 2B, 2C and 2D are each a diagram illustrating an exemplary environment in which some embodiments may operate.

As shown in FIG. 2A, an AR display 200 may include concurrent presentation of a 3D virtual medical model 201 and a view of two physical instruments 202, 204 currently being used and held by a user. Each physical instrument 202, 204 includes respective codes 202-1, 202-2, 204-1, 204-2. According to some embodiments, the codes 202-1, 202-2, 204-1, 204-2 may be fiducial markers that can be tracked by the Interaction Engine, such as via the AR display headset. For example, the AR display headset tracks each respective physical instrument 202, 204 according to the visual movement of each instrument's corresponding codes 202-1, 202-2, 204-1, 204-2. The Interaction Engine further determines a pose of the instrument 202, 204 based on current coordinates of the tracked codes 202-1, 202-2, 204-1, 204-2. In some embodiments, the codes 202, 204 may be passive or active infrared fiducial markers, barcodes or electromagnetic-visible markers.

The Interaction Engine initiates a virtual interaction mode for a particular physical instrument 202, 204 upon detecting that a view of all codes 202-1, 202-2, 204-1, 204-2 on that particular physical instrument is not obstructed. For example, as shown in FIG. 2A, each instrument 202, 204 has a corresponding code 202-2, 204-2 with an obstructed view resulting from the user placing a thumb on each code 202-2, 204-2. Due to the obstructed views of the codes 202-2, 204-2, the Interaction Engine will not initiate a virtual interaction mode for either instrument 202, 204

Figure 2B:
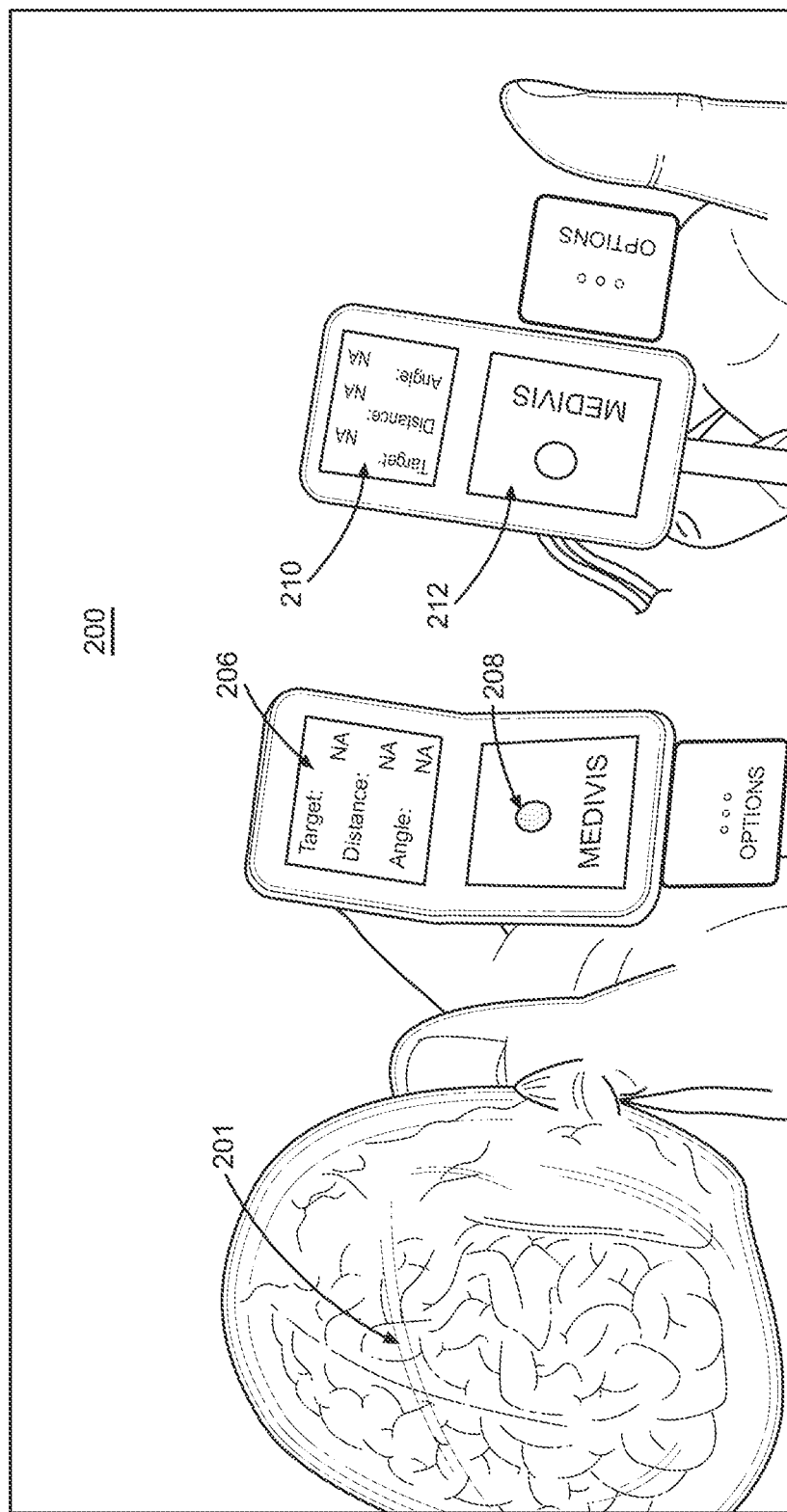

As shown in FIG. 2B, based on detecting one or more physical gestures based on the user removing each thumb away from obstructing the corresponding code 202-2, 204-2, the Interaction Engine initiates the virtual interaction mode with respect to both instruments 202, 204. In other embodiments, the Interaction Engine initiates a virtual interaction mode based on a code(s) 202-2, 204-2 being visible such that it is in view of a camera(s) on the AR display headset device. The Interaction Engine generates virtual overlays 206, 208, 210, 212 to be aligned with and displayed over the codes 202-1, 202-2, 204-1, 204-2. The Interaction Engine determines display positions for the virtual overlays 206, 208, 210, 212 based on the current positional coordinates of the codes 202-1, 202-2, 204-1, 204-2. In addition, the Interaction Engine generates a virtual object(s) comprising a virtual overlay for a portion(s) of the physical instrument. For example, the Interaction Engine generates and renders a virtual overlay over all portions of the physical instrument's body that are viewable from the AR headset device (i.e. AR display headset device).

A first type of virtual overlay 206, 210 may display real-time data related to a physical instrument pose (i.e. instrument pose data) with respect to a virtual target object displayed in the AR display 200. A second type of virtual overlay 208, 212 may display a colored status indicator of the physical instrument 202, 204. For example, a virtual overlay 208 may have a green colored status indicator and the other virtual overlay 212 may have a red colored status indicator. In some embodiments, a green colored status indicator represents that the corresponding physical instrument, upon which the green colored status indicator is overlayed, is an active physical instrument providing input data with respect to a virtual interaction. A red colored status indicator represents that the corresponding physical instrument, upon which the red colored status indicator is overlayed, is an inactive physical instrument that is not providing input data with respect to a virtual interaction. That is, the Interaction Engine will not identifying one or more physical gestures performed by the user with an inactive physical instrument as representing real-time input data associated with a virtual interaction.

Figure 2C:
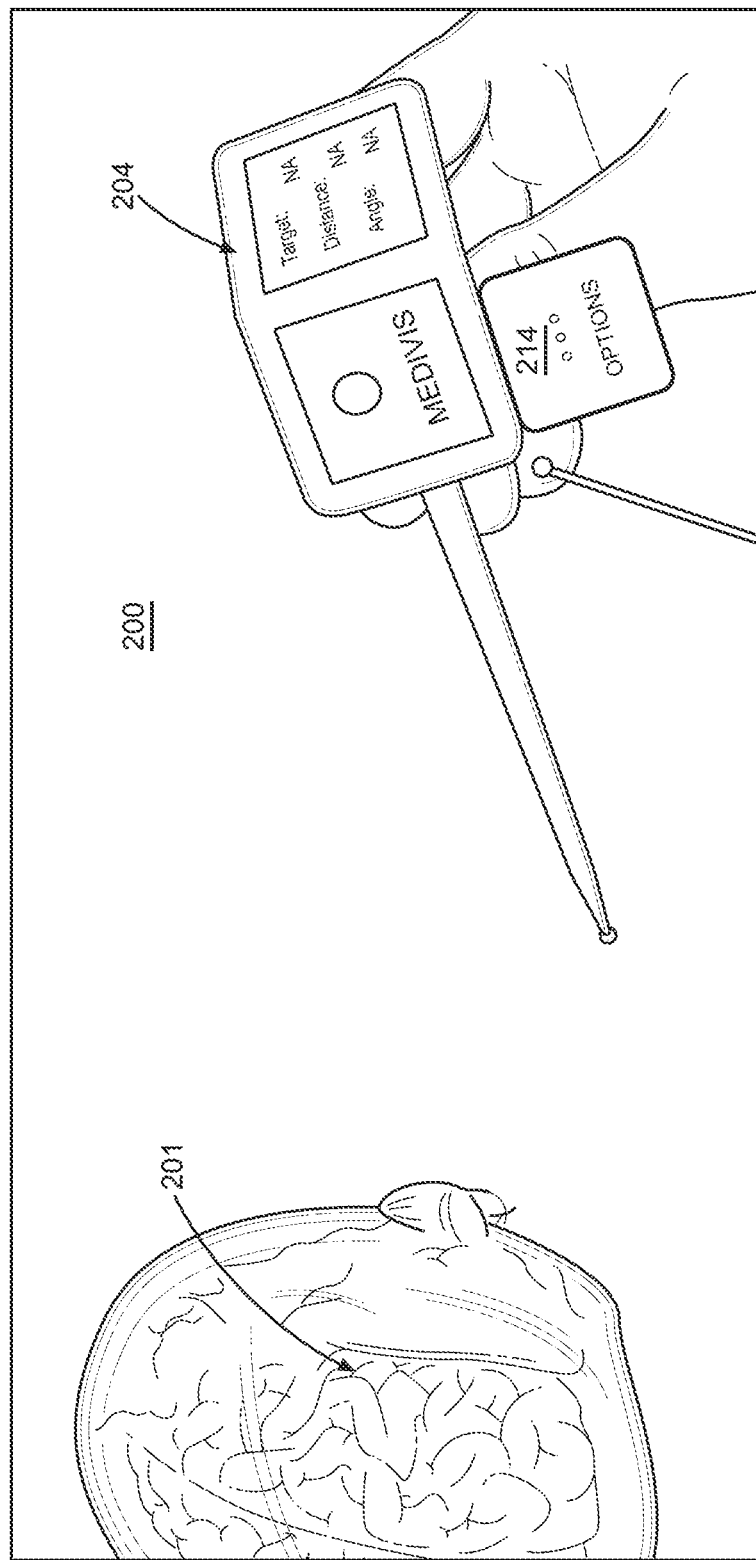

As shown in FIG. 2C, the Interaction Engine appends a third type of virtual overlay 214 to a current display of a physical instrument 204 and may create a highlighting effect to be displayed at the tip of the physical instrument 205. According to some embodiments, the virtual overlay 214 may be an expandable and collapsible menu. The Interaction Engine tracks a physical gesture performed by the user with respect to the virtual overlay 214. For example, the Interaction Engine may generate directional data based on the user's hands moving towards and proximate to the virtual overlay 214. In addition, the Interaction Engine may detect a selection physical gesture applied to the virtual overlay 214. The selection physical gesture may be based on the user positioning a fingertip at a coordinate(s) that maps to a display position of the virtual overlay 214. In some embodiments, the selection physical gesture may be based on movement of a fingertip(s) across (or over) a rendered virtual overlay 214.

Figure 2D:
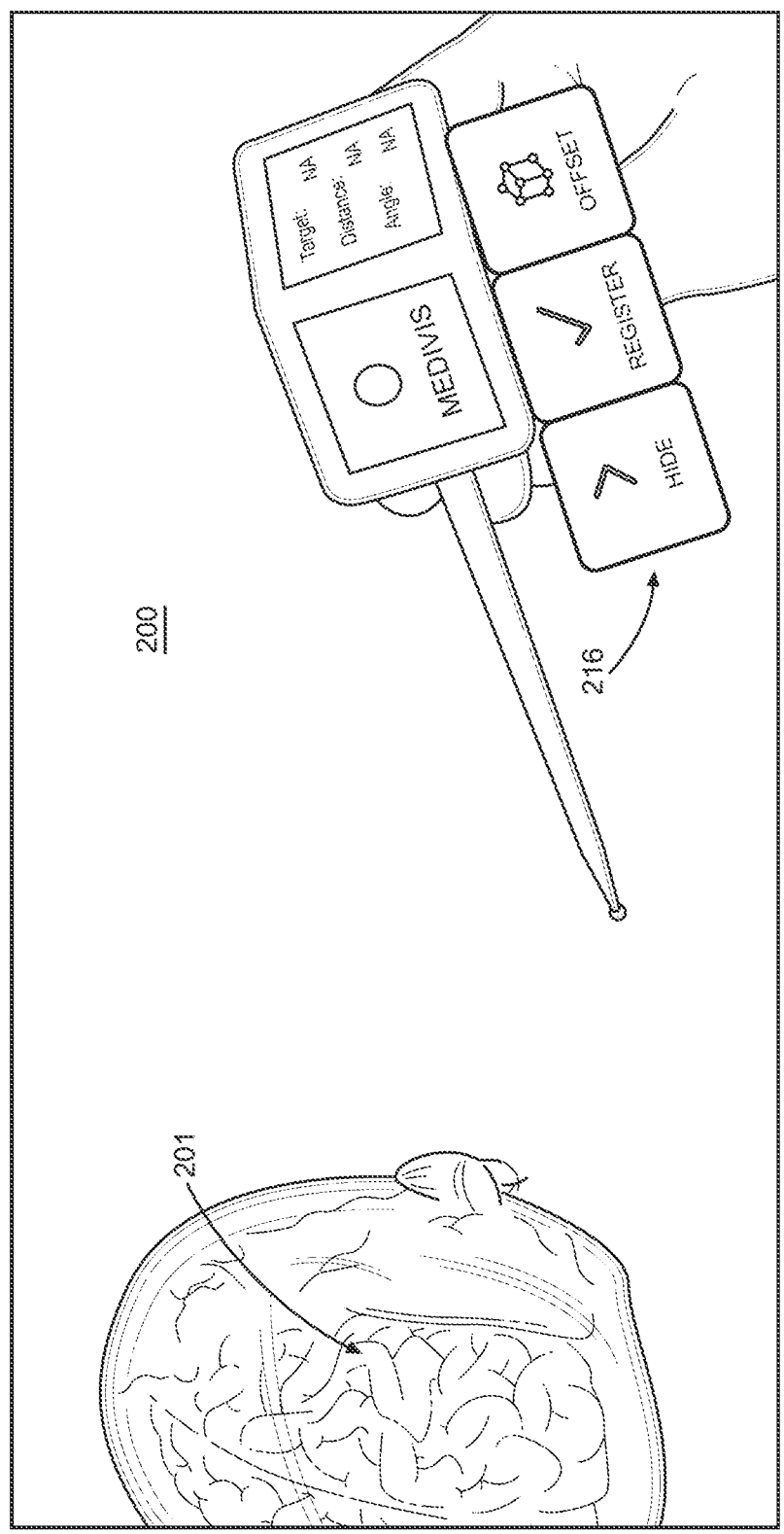

As shown in FIG. 2D, upon detection of the selection of the virtual overlay 214, the Interaction Engine expands the virtual overlay 214 to present a rendering of an expanded virtual menu 216.

Figure 3:
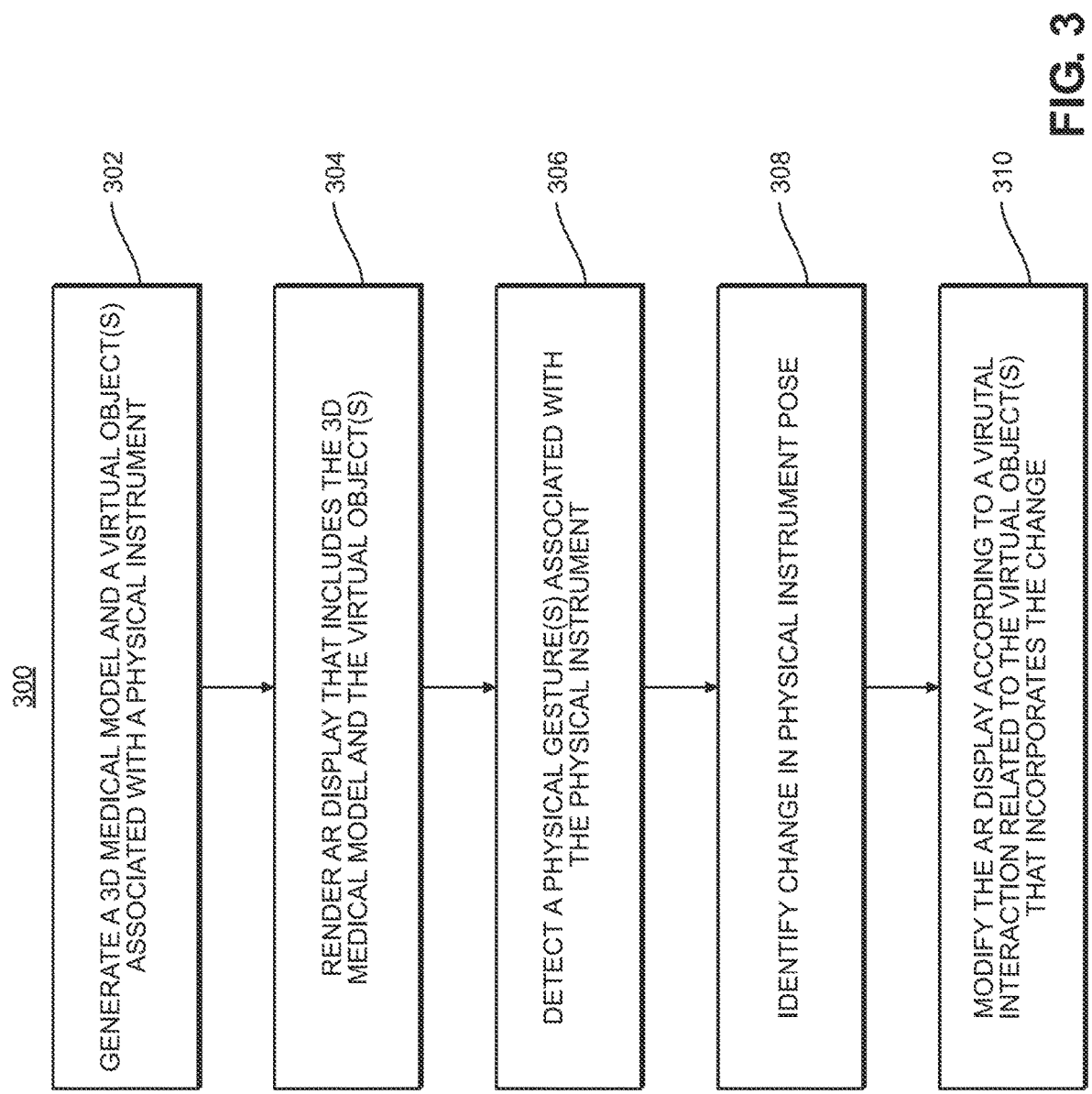
FIG. 3 is a diagram illustrating an exemplary method that may be performed in some embodiments.

As shown in flowchart 300 of FIG. 3, the Interaction Engine generates, within a unified 3D coordinate space: a 3D virtual medical model positioned according to a model pose and at least one virtual object associated with a physical instrument, where the physical instrument has a current instrument pose. (Act 302) Respective physical instrument poses are based at least on current coordinates of one or more fiducial markers disposed on the physical instrument, in the unified 3D coordinate space.

The Interaction Engine renders an AR display that includes concurrent display of the 3D virtual medical model and the virtual object(s). (Act 304) The Interaction Engine detects one or more physical gestures associated with the physical instrument. (Act 306)

The Interaction Engine identifies a change related to the current physical instrument pose in the unified 3D coordinate space, due to at least one of the detected physical gestures associated with the physical instrument. (Act 308) The Interaction Engine modifies the AR display according to a virtual interaction related to the virtual object(s) that incorporates the change of the current physical instrument pose. (Act 310)

Figure 4:
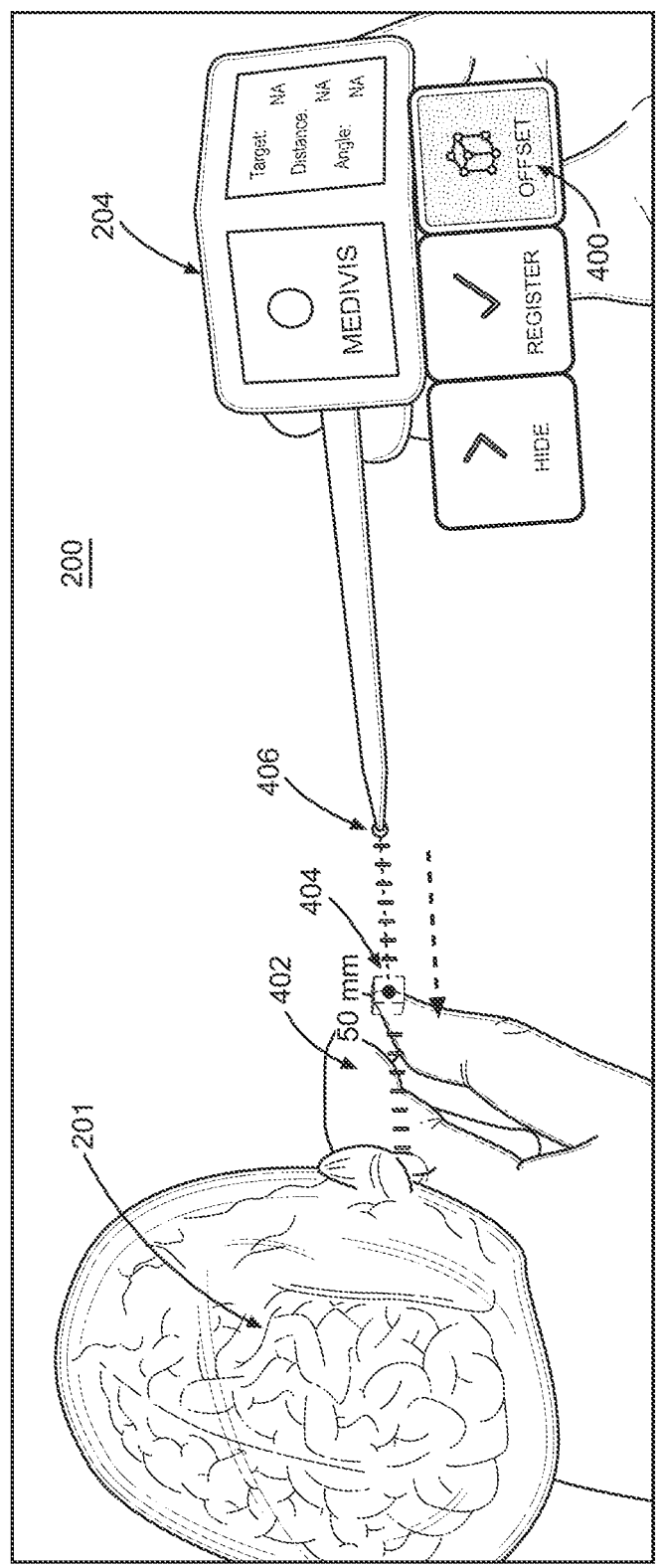
FIG. 4 is a diagram illustrating an exemplary environment in which some embodiments may operate.

As shown in FIG. 4, the Interaction Engine provides functionality for an offset tip virtual interaction with respect to the physical instrument 204. The Interaction Engine initiates the offset tip virtual interaction in response to detecting selection of an offset functionality indicator 400 displayed in an expanded virtual menu 216. The Interaction Engine identifies respective hand joint position changes occurring proximate to coordinates of a current position of a physical tip 406 of a physical instrument 204. For example, the Interaction Engine may identify the respective hand joint position changes as representative of a pinch physical gesture 402 performed by a user's hand at coordinates that correspond to the display position of the physical tip 406.

Subsequent to detection of the pinch physical gesture, the Interaction Engine may determine directional data based on tracking movement of the user's pinched hand 406 relative to the display position of the physical tip 406. For example, the user's hand 406 may move away from the display position of the physical tip 406 and complete the movement at a display position with a particular distance away from the physical tip 406.

The Interaction Engine may determine that a range of time has expired as measured from completion of the hand movement away from the display position 406. Upon expiration of the range of time, the Interaction Engine determines a virtual offset tip position 404 for the physical instrument 204 proximate to the display position of the user's hand when the range of time expired. The Interaction Engine modifies the AR display 200 by generating display of a virtual extension of the physical instrument from the tip position 406 to the virtual offset tip position 404. In some embodiments, a current distance amount (for example: "50 mm") between the virtual offset tip position 404 and a display position of the physical tip 406 may be displayed proximate to a rendering of a virtual offset tip. In addition, the Interaction Engine renders and displays a series of virtual dashes extending from the position of the physical tip 406. The series of virtual dashes indicates a maximum allowable distance between the virtual offset tip position 404 and a display position of the physical tip 406. It is understood that the virtual offset tip and a virtual offset extending from the position of the physical tip 406 are virtual objects.

Figure 5A:
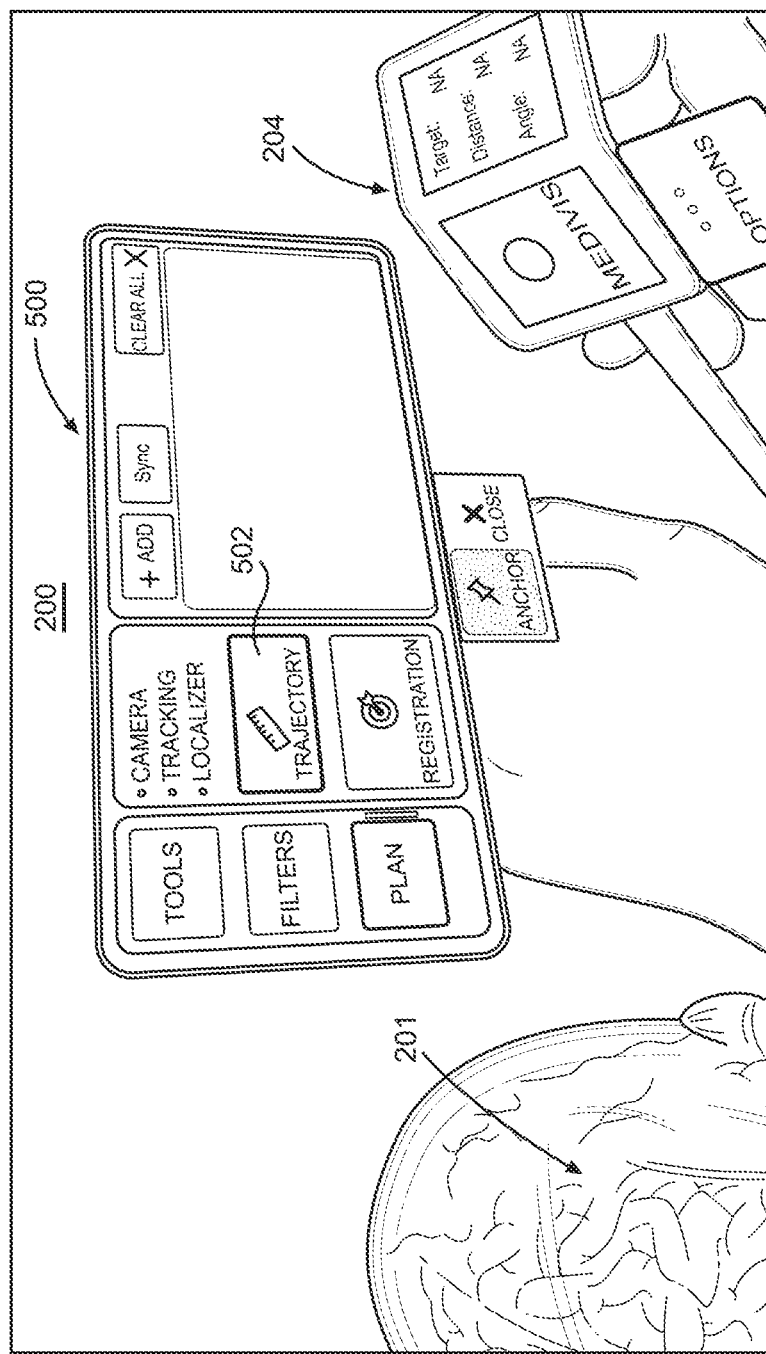
FIGS. 5A, 5B, 5C and 5D are each a diagram illustrating an exemplary environment in which some embodiments may operate.

As shown in FIG. 5A, the Interaction Engine provides functionality for a trajectory virtual interaction with respect to the physical instrument 204. According to various embodiments, the Interaction Engine displays a virtual menu 500 in the AR display 200. The virtual menu 500 may include a plurality of selectable virtual functionalities. For example, a selectable virtual functionality 502 may be selected by the user via a physical gesture with the user's hand or a predefined type of movement of the physical instrument 204. Selection of the virtual functionality 502 triggers initiation of a virtual trajectory planning workflow with respect to one or more virtual trajectory objects.

Figure 5B:
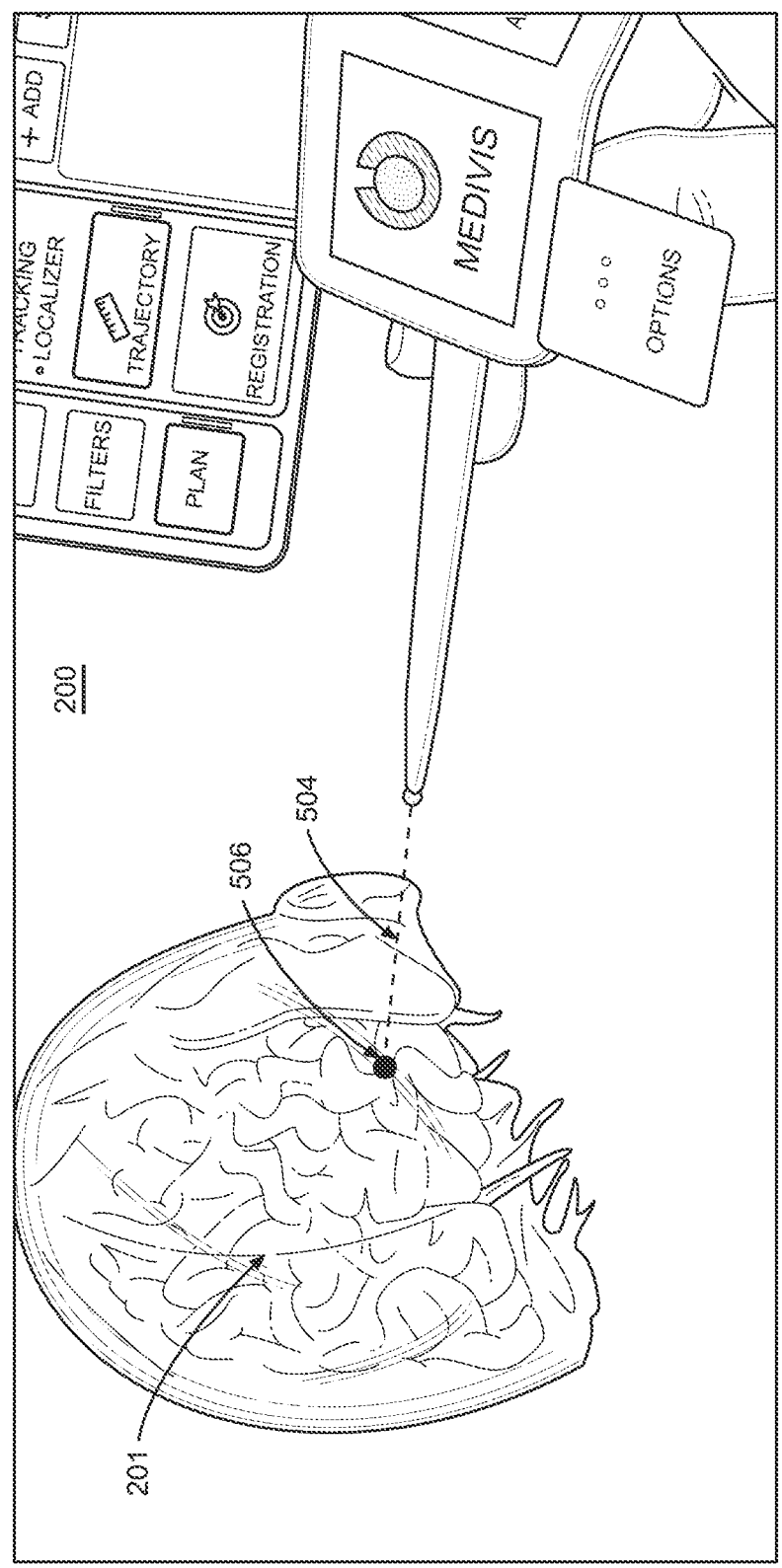

As shown in FIG. 5B, the Interaction Engine identifies selection of a target point 506 of a virtual trajectory by a virtual offset 504 displayed as an extension of the physical instrument. For example, the Interaction Engine tracks a physical gesture(s) with respect to the physical instrument that places the virtual offset tip at coordinates of a display position within a currently displayed 3D virtual medical model 201. The selected target point 506 thereby corresponds to a portion of the 3D virtual medical model 201. For example, the target point 506 may be a display position with particular coordinates that reference a particular internal anatomical location represented by the 3D virtual medical model.

Figure 5C:
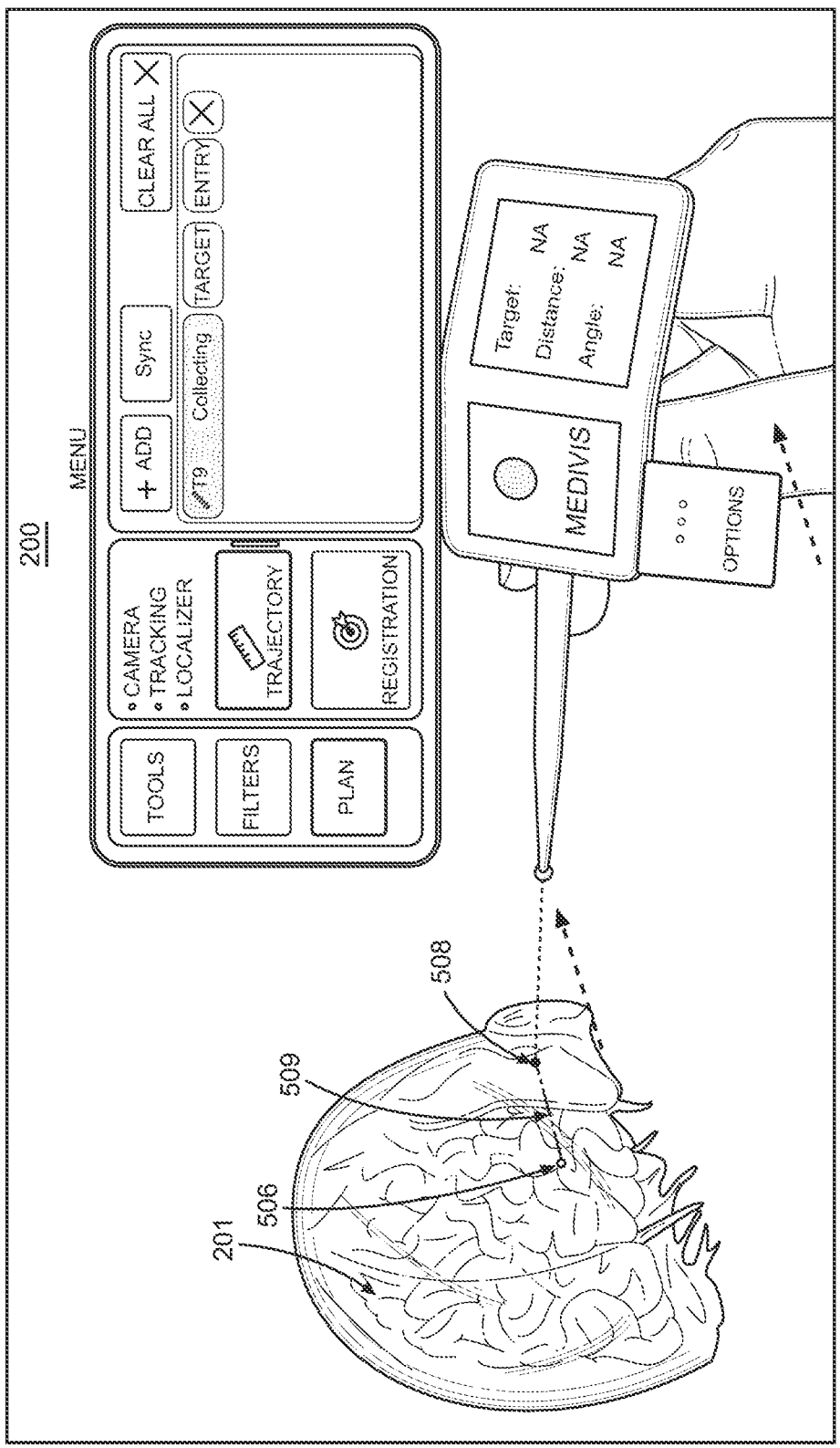

As shown in FIG. 5C, the Interaction Engine may determine directional data based on tracking movement of the virtual offset tip resulting from a physical gesture(s) that changes the current coordinates relative to a portion of the physical instrument. For example, the user's hand may move the physical instrument according to a particular direction such that display of the virtual offset tip by the Interaction Engine moves away from the selected target point 506. The Interaction Engine identifies selection of an entry point 508 that corresponds to a different portion of the 3D virtual medical model 201. For example, the entry point 508 may be a display position with particular coordinates that reference a particular external anatomical location (such as a skin surface location) represented by the 3D virtual medical model 201.

The Interaction Engine modifies the AR display 200 to include display of a virtual trajectory 509 that spans from the selected target point 506 to the selected entry point 508. The virtual trajectory 509 includes multiple sets of coordinates that occur between the selected target point 506 and the selected entry point 508. Each set of coordinates along the virtual trajectory 509 corresponds to a display position in the 3D virtual medical model 201. For example, each set of coordinates may be a display position with particular coordinates that reference a particular anatomical location represented by the 3D virtual medical model 201 that occurs along the displayed virtual trajectory 509 and between the selected points 506, 508. In some embodiments, the Interaction Engine generates and displays a virtual object comprising a virtual dashed extension of the virtual trajectory 509 that further extends beyond the entry point 508. In addition, the select points 506, 508 may also be virtual objects.

Figure 5D:
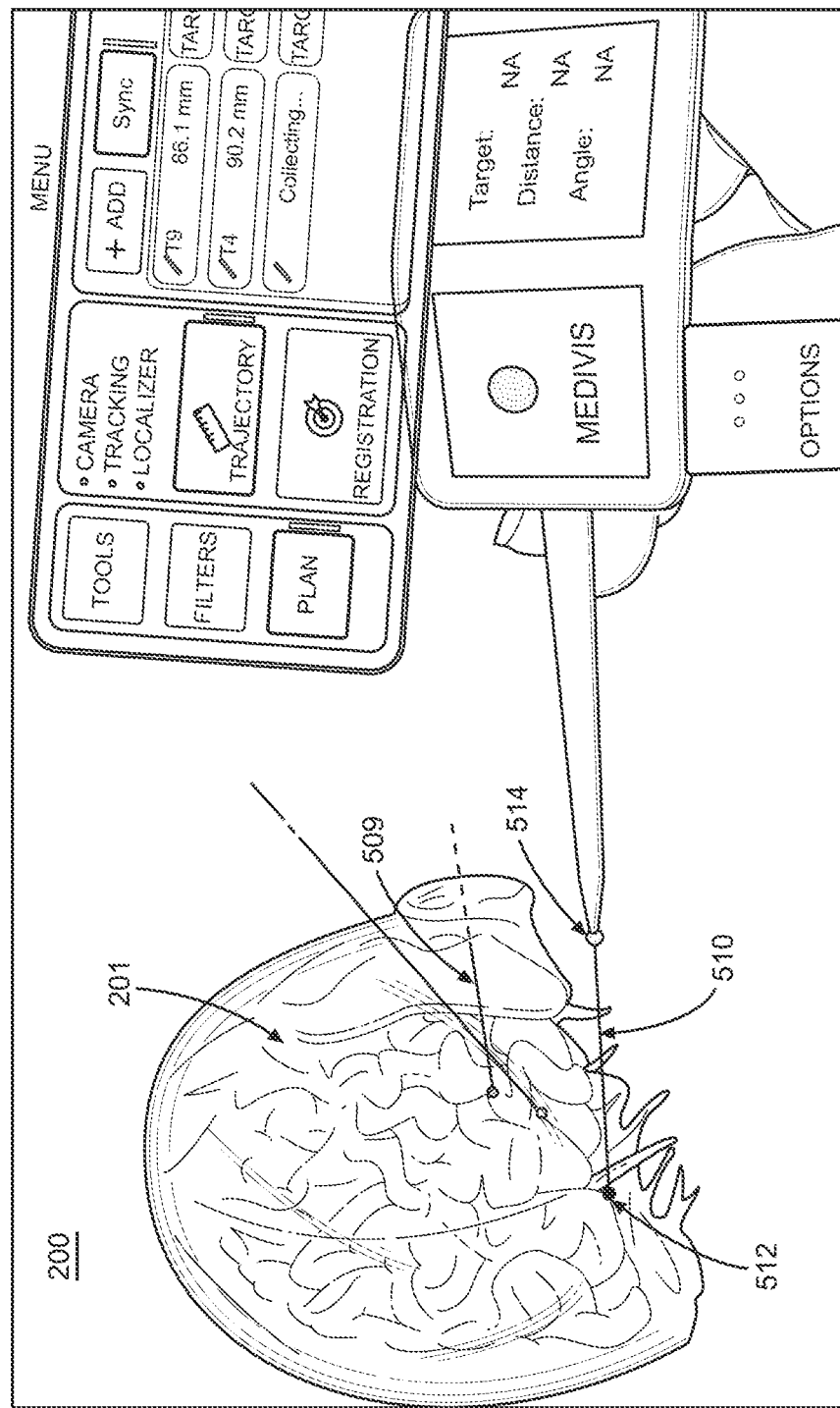

As shown in FIG. 5D, the Interaction Engine provides functionality for a trajectory virtual interaction with respect to the physical instrument. In some embodiments, the trajectory virtual interaction provides for synchronized trajectory collection. For example, the Interaction Engine may display a virtual object comprising a virtual offset 510 of the physical instrument. For example, the virtual offset 510 may be displayed as a line extending from the tip of the physical instrument 514 to a display position of a virtual object comprising the virtual offset tip 512. The Interaction Engine receives a selection that the virtual offset 510 in its entirety represents a span of a planned virtual trajectory. In some embodiments, the virtual offset tip 512 represents a target point and the physical tip 514 of the physical instrument represents an entry point.

Figure 6A:
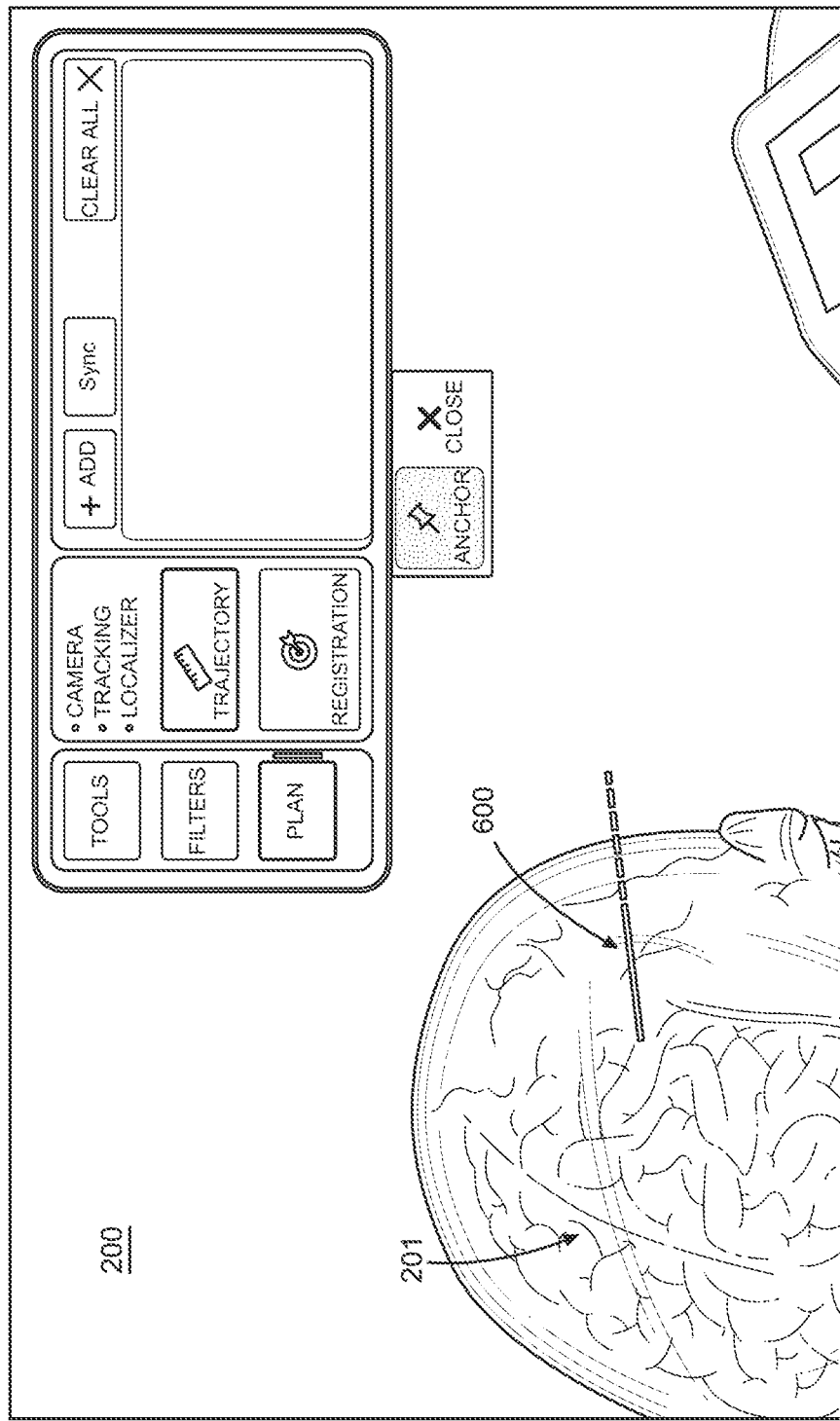
FIGS. 6A and 6B are each a diagram illustrating an exemplary environment in which some embodiments may operate.

As shown in FIG. 6A, the Interaction Engine provides functionality for a trajectory alignment virtual interaction with respect to the physical instrument. In various embodiments, the Interaction Engine displays a virtual object comprising a virtual trajectory 600 with respect to display coordinate positions that correspond to respective anatomical locations represented by the 3D virtual medical model 201.

Figure 6B:
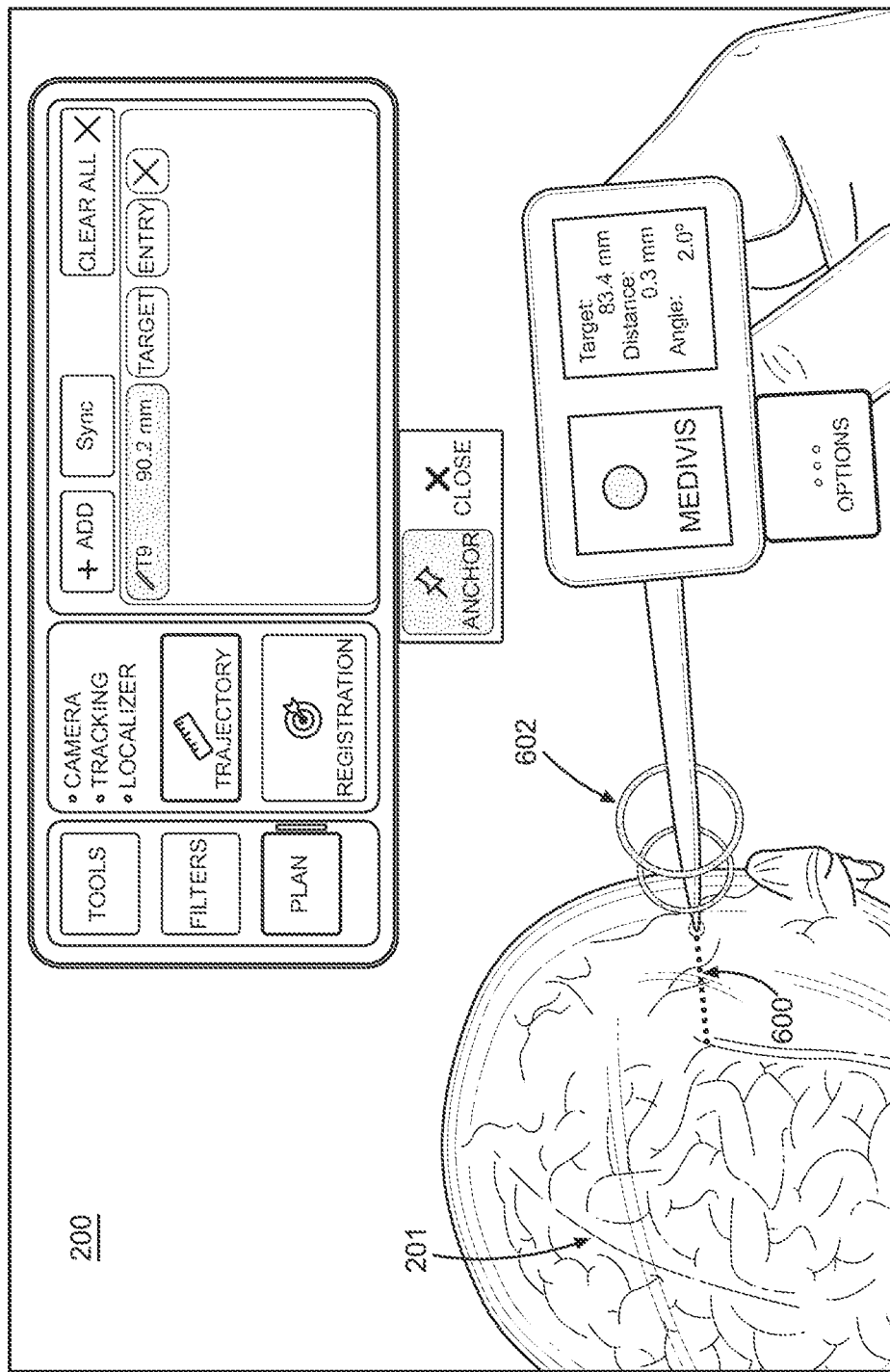

As shown in FIG. 6B, the Interaction Engine detects that the physical instrument's current pose (i.e. position and orientation) has been stable, for a particular threshold amount of time, at a current display coordinate position that is within a threshold proximate distance from a target point of the virtual trajectory 600. The Interaction Engine may further detect that a current pose of the physical instrument is within a threshold angular difference from a currently displayed virtual trajectory 600.

Based on detecting the positional and orientational differences between the physical instrument and the virtual trajectory 600 satisfy the respective threshold stabilities, the Interaction Engine displays a virtual trajectory alignment indicator 602 based on selection of a virtual menu functionality object that corresponds with the virtual trajectory alignment indicator object 602. The indicator 602 provides a visual indication that the current position and orientation of the physical instrument is in alignment with the planned virtual trajectory 600. For example, the virtual trajectory alignment indicator 602 may be a plurality of colored graphical rings that appear in the AR display 200 as surrounding a portion(s) of the physical instrument. In response to detecting alignment, Interaction Engine may change the color of the graphical rings associated with the indicator 602. The Interaction Engine may further display a directional indicator virtual object proximate or inside the alignment indicator 602 to provide a visual cue for assisting guidance of the physical instrument into alignment. Display of the directional indicator may be removed once alignment is detected. In some embodiments, the Interaction Engine may display a virtual graphical overlay object over a portion of the physical instrument itself. For example, the virtual graphical overlay may display real-time metric calculations (e.g. Target, Distance, Angle) related to a current relationship between the physical instrument's pose and the trajectory 600.

Figure 7A:
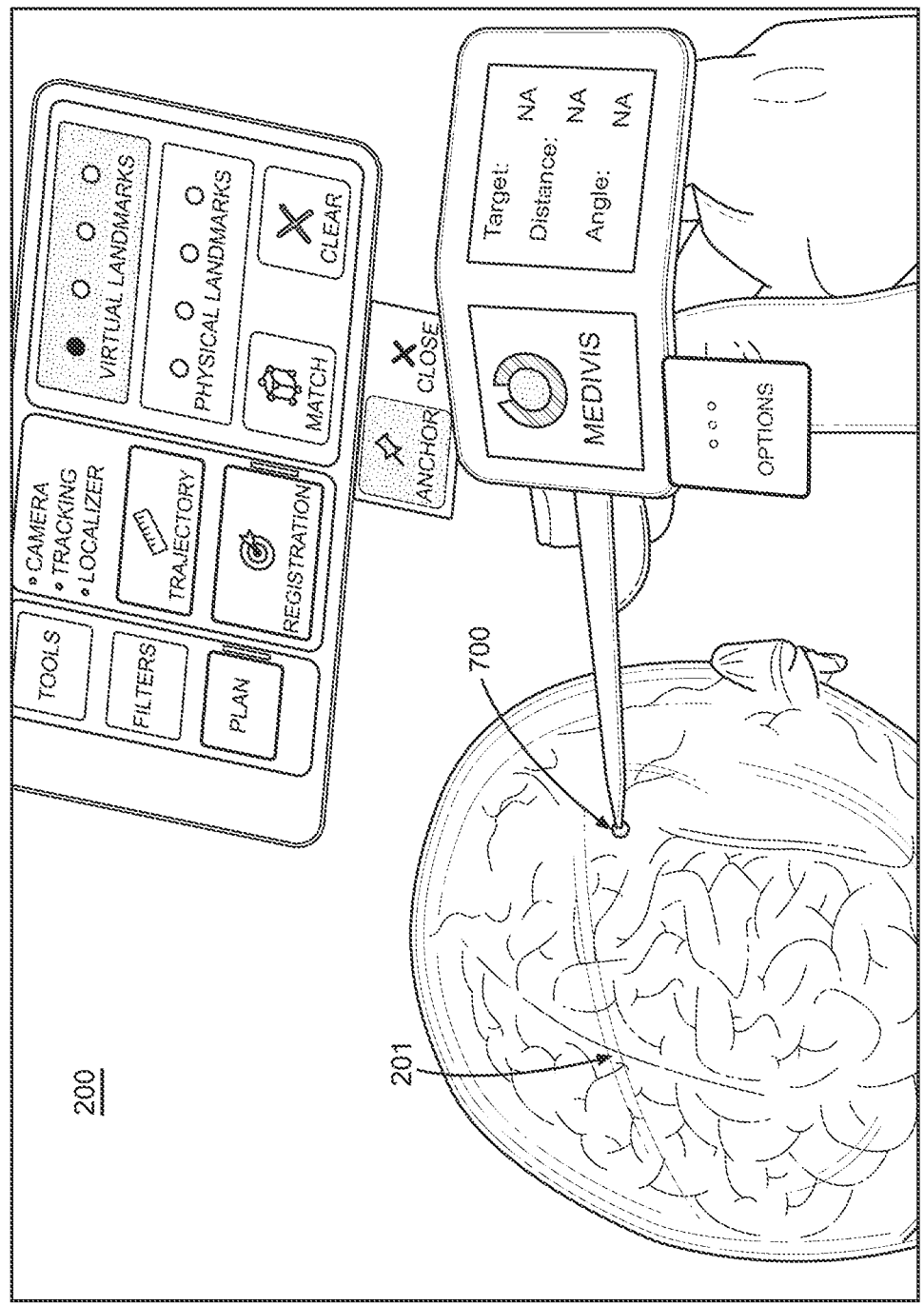
FIGS. 7A and 7B are each a diagram illustrating an exemplary environment in which some embodiments may operate.

As shown in FIG. 7A, the Interaction Engine provides functionality for a landmark registration virtual interaction with respect to the physical instrument. The Interaction Engine detects that the physical tip of the physical instrument has been stable, for a particular threshold amount of time, at a current display coordinate position. For example, stability of the physical tip may be based on detected stability of the physical instrument's pose. Based on the detected stability, the Interaction Engine selects the current display coordinate position of the tip of physical instrument as a first virtual landmark 700. The first virtual landmark 700 is a virtual object that corresponds to a first anatomical location represented by the 3D virtual medical model 201.

Figure 7B:
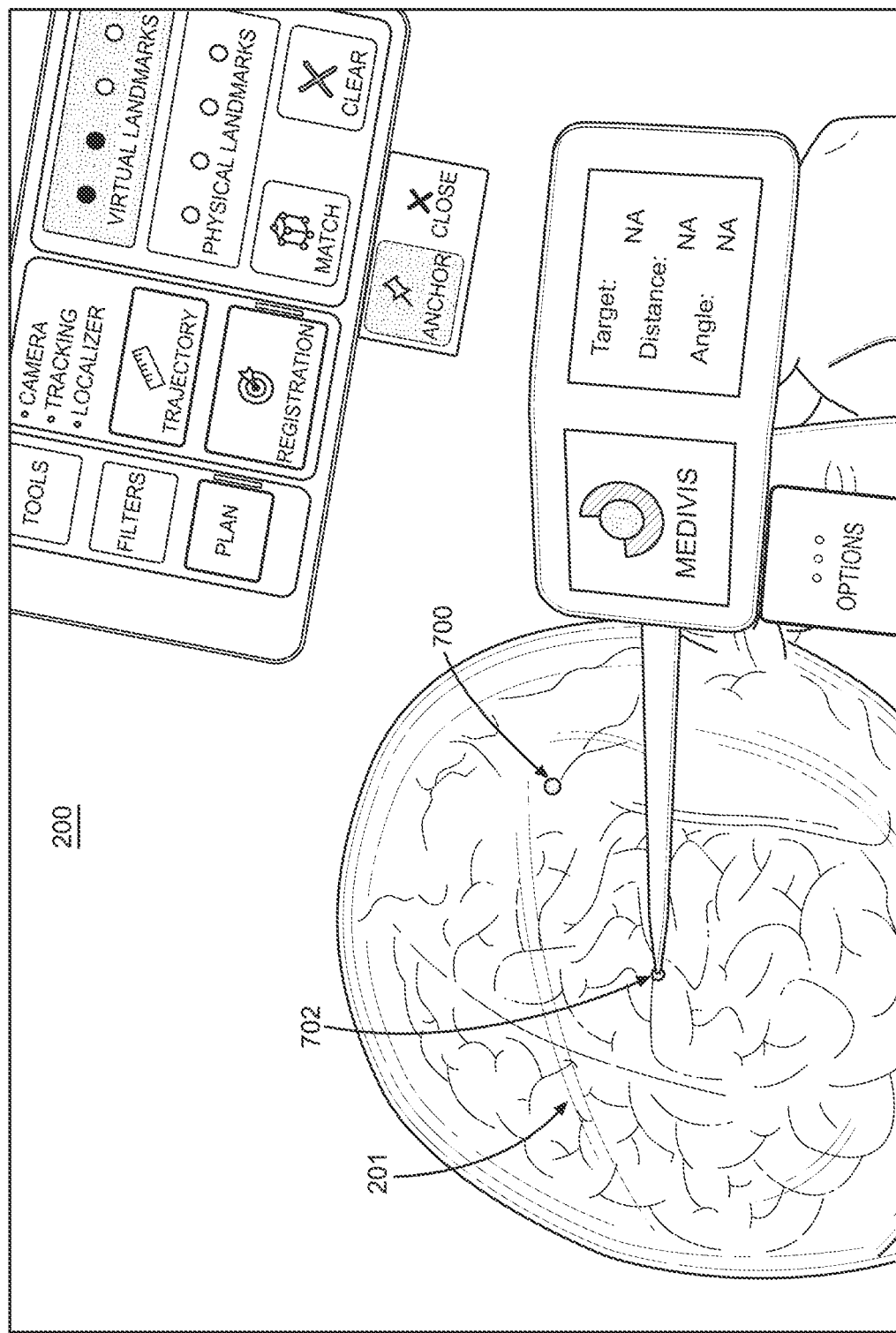

As shown in FIG. 7B, the Interaction Engine detects that the physical tip of the physical instrument has been stable, for a particular threshold amount of time, at a subsequent display coordinate position. Based on the detected stability, the Interaction Engine selects the subsequent display coordinate position of the physical tip of physical instrument as a second virtual landmark 702. The second virtual landmark 702 is a virtual object that corresponds to a second anatomical location represented by the 3D virtual medical model 201.

Upon receipt of selection of the second virtual landmark 702, the Interaction Engine updates the first virtual landmark 700 with a modified visual appearance. For example, the Interaction Engine updates the first virtual landmark 700 to be rendered in the AR display 200 in a color that is different than a color of the second virtual landmark 702. In other embodiments, each successive virtual landmark may be associated with a predefined virtual object color such that modification of a landmark's visual appearance is not affected by subsequent virtual landmarks.

In various embodiments, one or more physical landmarks may be similarly collected as virtual landmarks. For example, the Interaction Engine detects selection of a physical landmark(s) with respect to a location of a physical, anatomical area. Each location of a physical landmark may be represented according to fixed coordinates in the unified 3D space. That is, a physical landmark is a fixed location in the unified 3D space, while a virtual landmark represents a location within the 3D virtual medical model 201. The Interaction Engine further modifies the AR display by display of a visual indicator for each physical landmark. Each visual indicator of a virtual landmark is displayed at a display position based on the coordinates of the anatomical location within the 3D virtual medical model 201. It is understood that the Interaction Engine may concurrently display virtual and physical landmarks. In addition, the Interaction Engine may display a virtual landmark in alignment with a display of a corresponding physical landmark.

According to various embodiments, the Interaction Engine fixes (i.e. anchors, sets, maintains) the display of a physical landmark visual indicator at a display position based on the coordinates of the corresponding physical anatomical location. For a user wearing an AR headset device, the Interaction Engine maintains the user's view of the physical landmark visual indicator at the corresponding physical anatomical location as the user moves and the Interaction Engine detect changes in the pose of the AR headset device. However, the Interaction Engine may update a display position of a virtual landmark indicator based on a change of a model pose of a model that changes the user's perspective view of the anatomical location on the 3D virtual medical model 201 that corresponds with the virtual landmark indicator.

Figure 8A:
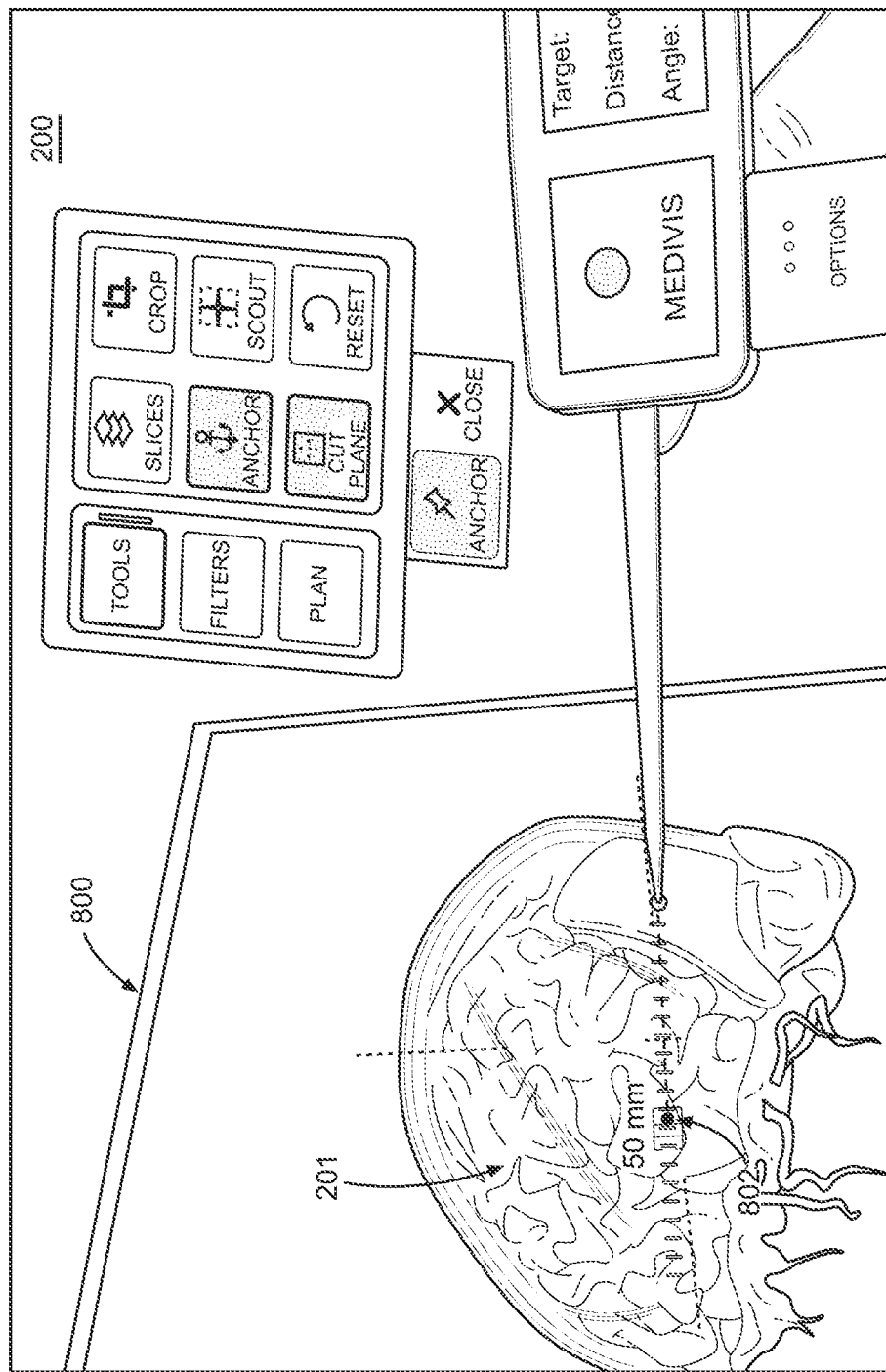
FIGS. 8A and 8B are each a diagram illustrating an exemplary environment in which some embodiments may operate.

As shown in FIG. 8A, the Interaction Engine provides functionality for a clipping plane virtual interaction with respect to the physical instrument. The Interaction Engine displays a virtual object comprising a clipping plane 800 concurrently with the 3D virtual medical model 201 in the AR display 200. The Interaction Engine may detect selection of the clipping plane 800. For example, one or more physical gestures may update and adjust the current pose of the physical instrument such that the coordinates for the display position of the virtual offset tip 802 overlaps with a coordinate display position of a portion of the clipping plane 800. It is understood that the various coordinates associated with the clipping plane 800 include coordinates bounded within the clipping pane 800. In some embodiments, the clipping plane 800 may also be referred to as a virtual object cut plane (i.e. "cut plane").

Figure 8B:
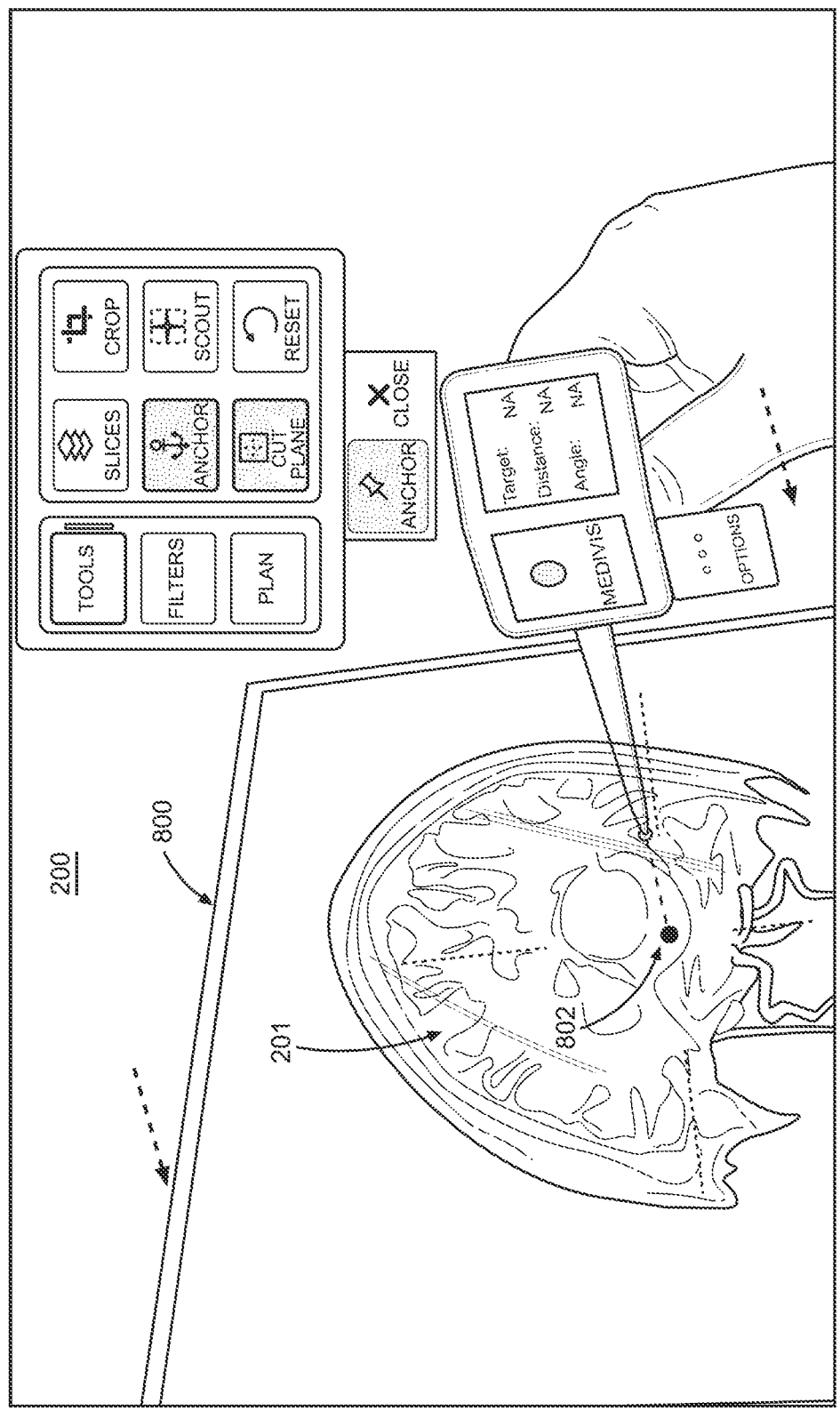

As shown in FIG. 8B, the Interaction Engine displays the clipping plane 800 at a display position as a result of the clipping plane 800 being moved by respective physical gestures associated with the physical instrument. The Interaction Engine may represent movement of the clipping plane 800 based on movement of the physical instrument and/or respective changes to the physical instrument's pose. For example, the Interaction Engine renders movement of the clipping plane 800 towards the 3D virtual medical model 201 as the coordinates for the display position of the virtual offset tip 802 and the position and orientation of (i.e. instrument pose data) of the physical instrument represents movement toward coordinates associated with display positions of various portions of the 3D virtual medical model 201. It is understood that, in some embodiments, the clipping plane 800 is rendered to be perpendicular to a current physical instrument pose.

Due to the movement of the clipping plane 800, the Interaction Engine determines that various coordinates bounded within the clipping plane 800 overlap with coordinates associated with one or more portions of the 3D virtual medical model 201. For example, the Interaction Engine detects that an updated display position of the clipping plane 800 overlaps with coordinates that also correspond to anatomical locations represented by the 3D virtual medical model 201. The Interaction Engine updates the 3D virtual medical model 201 displayed in the AR display 200 to include portrayal of medical model data of the 3D virtual medical model 201 associated with the overlapping coordinates.

Figure 9:
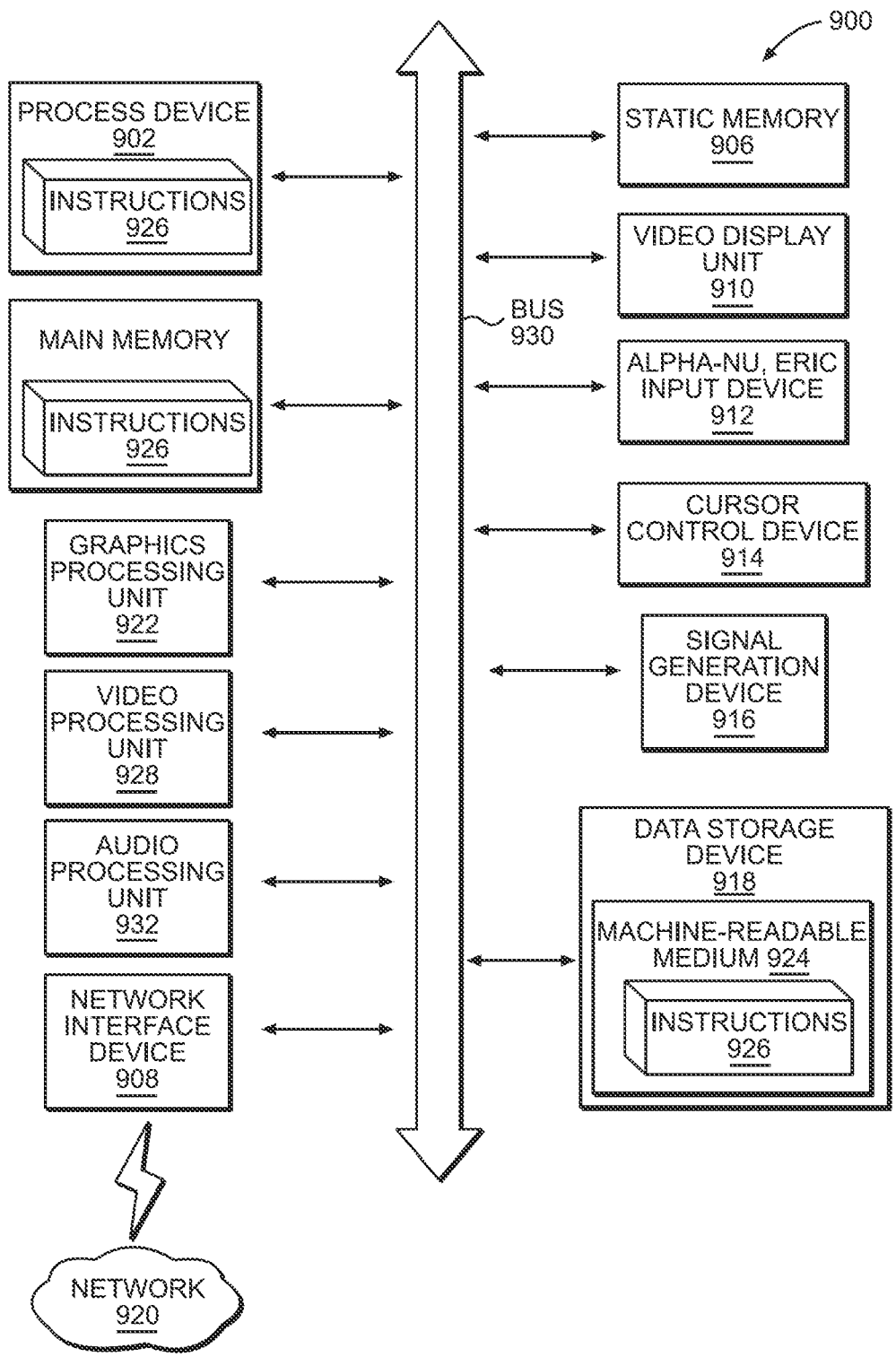
FIG. 9 is a diagram illustrating an exemplary environment in which some embodiments may operate.

FIG. 9 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 900 includes a processing device 902, a main memory 904 (e.g., read-only memory (ROM), flash memory, dynamic random access memory (DRAM) such as synchronous DRAM (SDRAM) or Rambus DRAM (RDRAM), etc.), a static memory 906 (e.g., flash memory, static random access memory (SRAM), etc.), and a data storage device 918, which communicate with each other via a bus 930.

Processing device 902 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. The processing device 902 is configured to execute instructions 926 for performing the operations and steps discussed herein.

The computer system 900 may further include a network interface device 908 to communicate over the network 920. The computer system 900 also may include a video display unit 910 (e.g., a liquid crystal display (LCD) or a cathode ray tube (CRT)), an alphanumeric input device 912 (e.g., a keyboard), a cursor control device 914 (e.g., a mouse), a graphics processing unit 922, a signal generation device 916 (e.g., a speaker), graphics processing unit 922, video processing unit 928, and audio processing unit 932.

The data storage device 918 may include a machine-readable storage medium 924 (also known as a computer-readable medium) on which is stored one or more sets of instructions or software 926 embodying any one or more of the methodologies or functions described herein. The instructions 926 may also reside, completely or at least partially, within the main memory 904 and/or within the processing device 902 during execution thereof by the computer system 900, the main memory 904 and the processing device 902 also constituting machine-readable storage media.

In one implementation, the instructions 926 include instructions to implement functionality corresponding to the components of a device to perform the disclosure herein. While the machine-readable storage medium 924 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:
   generating within a unified three-dimensional (3D) coordinate space:
   (i) a 3D virtual medical model positioned according to a model pose; and
   (ii) at least one virtual object associated with a physical instrument, the physical instrument having a current instrument pose based at least on current coordinates of one or more fiducial markers disposed on the physical instrument, in the unified 3D coordinate space;
   rendering an Augmented Reality (AR) display that includes concurrent display of the 3D virtual medical model and the virtual object;
   detecting one or more physical gestures associated with the physical instrument;
   identifying a change related to the physical instrument pose, in the unified 3D coordinate space, due to at least one of the detected physical gestures associated with the physical instrument; and modifying the AR display according to at least one virtual interaction related to the virtual object that incorporates the change of the physical instrument pose, wherein modifying the AR display comprises: modifying the AR display by:
(i) generating a virtual trajectory of the physical instrument based on a target point at an internal anatomical location represented by the 3D virtual medical model and an entry point of the 3D virtual medical model;
(ii) displaying the virtual trajectory of the physical instrument in relation to the target point; and
(iii) displaying a visual indicator providing a first visual cue indicating the virtual trajectory of the physical instrument in currently misaligned with a planned virtual trajectory and a second visual cue upon determining the virtual trajectory of the physical instrument has moved into an alignment with the planned virtual trajectory.

2. The computer-implemented method of claim 1, wherein the entry point comprises a location of an exposed anatomical surface represented by the 3D virtual medical model.

3. The computer-implemented method of claim 1, wherein generating the virtual trajectory further comprises:
generating a portion of the virtual trajectory defined according to a span within the 3D virtual medical model between entry point and the target point.

4. The computer-implemented method of claim 3, wherein modifying the AR display further comprises:
concurrently displaying the portion of the virtual trajectory defined according to the span with display of the 3D virtual medical model.

5. The computer-implemented method of claim 3, wherein generating the virtual trajectory further comprises:
generating the portion of the virtual trajectory defined according to the span according to a first type of visual attribute; and
generating another portion of the virtual trajectory defined outside of the span according to a second type of visual attribute, the first type of visual attribute different than the second type of visual attribute.

6. A system comprising one or more processors, and a non-transitory computer-readable medium including one or more sequences of instructions that, when executed by the one or more processors, cause the system to perform operations comprising:
generating within a unified three-dimensional (3D) coordinate space:
(i) a 3D virtual medical model positioned according to a model pose; and
(ii) at least one virtual object associated with a physical instrument, the physical instrument having a current instrument pose based at least on current coordinates of one or more fiducial markers disposed on the physical instrument, in the unified 3D coordinate space;
rendering an Augmented Reality (AR) display that includes concurrent display of the 3D virtual medical model and the virtual object;
detecting one or more physical gestures associated with the physical instrument;
identifying a change related to the physical instrument pose, in the unified 3D coordinate space, due to at least one of the detected physical gestures associated with the physical instrument; and
modifying the AR display according to at least one virtual interaction related to the virtual object that incorporates the change of the physical instrument pose, wherein modifying the AR display comprises: modifying the AR display by:
(i) generating a virtual trajectory of the physical instrument based on a target point at an internal anatomical location represented by the 3D virtual medical model and an entry point of the 3D virtual medical model;
(ii) displaying the virtual trajectory of the physical instrument in relation to the target point; and
(iii) displaying a visual indicator providing a first visual cue indicating the virtual trajectory of the physical instrument in currently misaligned with a planned virtual trajectory and a second visual cue upon determining the virtual trajectory of the physical instrument has moved into an alignment with the planned virtual trajectory.

7. The system of claim 6, wherein the entry point comprises a location of an exposed anatomical surface represented by the 3D virtual medical model.

8. The system of claim 6, wherein generating the virtual trajectory further comprises:
generating a portion of the virtual trajectory defined according to a span within the 3D virtual medical model between entry point and the target point.

9. The system of claim 8, wherein modifying the AR display further comprises:
concurrently displaying the portion of the virtual trajectory defined according to the span with display of the 3D virtual medical model.

10. The system claim 8, wherein generating the virtual trajectory further comprises:
generating the portion of the virtual trajectory defined according to the span according to a first type of visual attribute; and
generating another portion of the virtual trajectory defined outside of the span according to a second type of visual attribute, the first type of visual attribute different than the second type of visual attribute.

11. A computer program product ("product") comprising a non-transitory computer-readable medium having a computer-readable program code embodied therein to be executed by one or more processors, the program code including instructions to:
generating within a unified three-dimensional (3D) coordinate space:
(i) a 3D virtual medical model positioned according to a model pose; and
(ii) at least one virtual object associated with a physical instrument, the physical instrument having a current instrument pose based at least on current coordinates of one or more fiducial markers disposed on the physical instrument, in the unified 3D coordinate space;
rendering an Augmented Reality (AR) display that includes concurrent display of the 3D virtual medical model and the virtual object;
detecting one or more physical gestures associated with the physical instrument;
identifying a change related to the physical instrument pose, in the unified 3D coordinate space, due to at least one of the detected physical gestures associated with the physical instrument; and
modifying the AR display according to at least one virtual interaction related to the virtual object that incorporates the change of the physical instrument pose, wherein modifying the AR display comprises: modifying the AR display by:
(i) generating a virtual trajectory of the physical instrument based on a target point at an internal anatomical location represented by the 3D virtual medical model and an entry point of the 3D virtual medical model;
(ii) displaying the virtual trajectory of the physical instrument in relation to the target point; and
(iii) displaying a visual indicator providing a first visual cue indicating the virtual trajectory of the physical instrument in currently misaligned with a planned virtual trajectory and a second visual cue upon determining the virtual trajectory of the physical instrument has moved into an alignment with the planned virtual trajectory.

12. The product of claim 11, wherein, wherein the entry point comprises a location of an exposed anatomical surface represented by the 3D virtual medical model.

13. The product of claim 11, wherein generating the virtual trajectory further comprises:
generating a portion of the virtual trajectory defined according to a span within the 3D virtual medical model between entry point and the target point.

14. The product of claim 13, wherein modifying the AR display further comprises:
concurrently displaying the portion of the virtual trajectory defined according to the span with display of the 3D virtual medical model; and
wherein generating the virtual trajectory further comprises:
generating the portion of the virtual trajectory defined according to the span according to a first type of visual attribute; and
generating another portion of the virtual trajectory defined outside of the span according to a second type of visual attribute, the first type of visual attribute different than the second type of visual attribute.

* * * * *